US00PP31530P2

(12) United States Plant Patent
Olesen et al.

(10) Patent No.: US PP31,530 P2
(45) Date of Patent: Mar. 10, 2020

(54) *CLEMATIS* PLANT NAMED 'EVIPO101'

(50) Latin Name: *Clematis viticella*
Varietal Denomination: Evipo101

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

( * ) Notice: Subject to any disclaimer, the term of this patent is extended or adjusted under 35 U.S.C. 154(b) by 0 days.

(21) Appl. No.: 15/999,896

(22) Filed: Sep. 10, 2018

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 6/72
See application file for complete search history.

(56) References Cited

PUBLICATIONS

Poulsen Roser(http://www.poulsenroser.com/assortment/clematis-collections/boulevard/taromina.aspx). Retrieved from internet on Jun. 25, 2019.*

* cited by examiner

*Primary Examiner* — Keith O. Robinson

(57) ABSTRACT

A new *Clematis* plant with a compact growth habit, profuse, violet purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification: Genus: *Clematis*. Species: *Viticella*.

Variety denomination: 'Evipo101'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2006 and the resulting seeds were planted the following winter in a controlled environment in Guernsey, Channel Islands, United Kingdom. The new variety named 'Evipo101' originated as a single seedling from the stated cross.

The new *Clematis* plant may be distinguished from its female seed parent and male pollen parent by the following characteristics. The female seed parent grows to a height of 100 cm, while the new variety grows to a height of 60 to 80 cm. The male seed parent has an overall growth height of 100 cm, while the new variety grows to a height of 60 to 80 cm.

The objective of the hybridization of this *Clematis* plant was to create a new and distinct variety for nursery culture with unique qualities such as:

1. Uniform and abundant violet purple flowers;
2. Vigorous and compact growth, making the variety suitable for container culture; and
3. Improved disease resistance.

This combination of qualities was lacking in *Clematis* plants that were in commercial cultivation and the qualities have been substantially achieved in the new variety.

'Evipo101' was selected by Mogens N. Olesen and Raymond J. Evison in their *Clematis* development program in the Channel Islands, United Kingdom in 2007. Asexual reproduction of 'Evipo101' by means of vegetative stem cuttings and traditional layering was first performed by Mogens N. Olesen and Raymond J. Evison in the nursery during the summer of 2007. This initial and subsequent asexual propagations have demonstrated that the characteristics of 'Evipo101' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo101'.

Specifically illustrated in FIG. 1 of the drawings is an open flower, tepals detached showing reproductive flower parts, flower buds at various stages of development, and a seed head.

Figure 1:
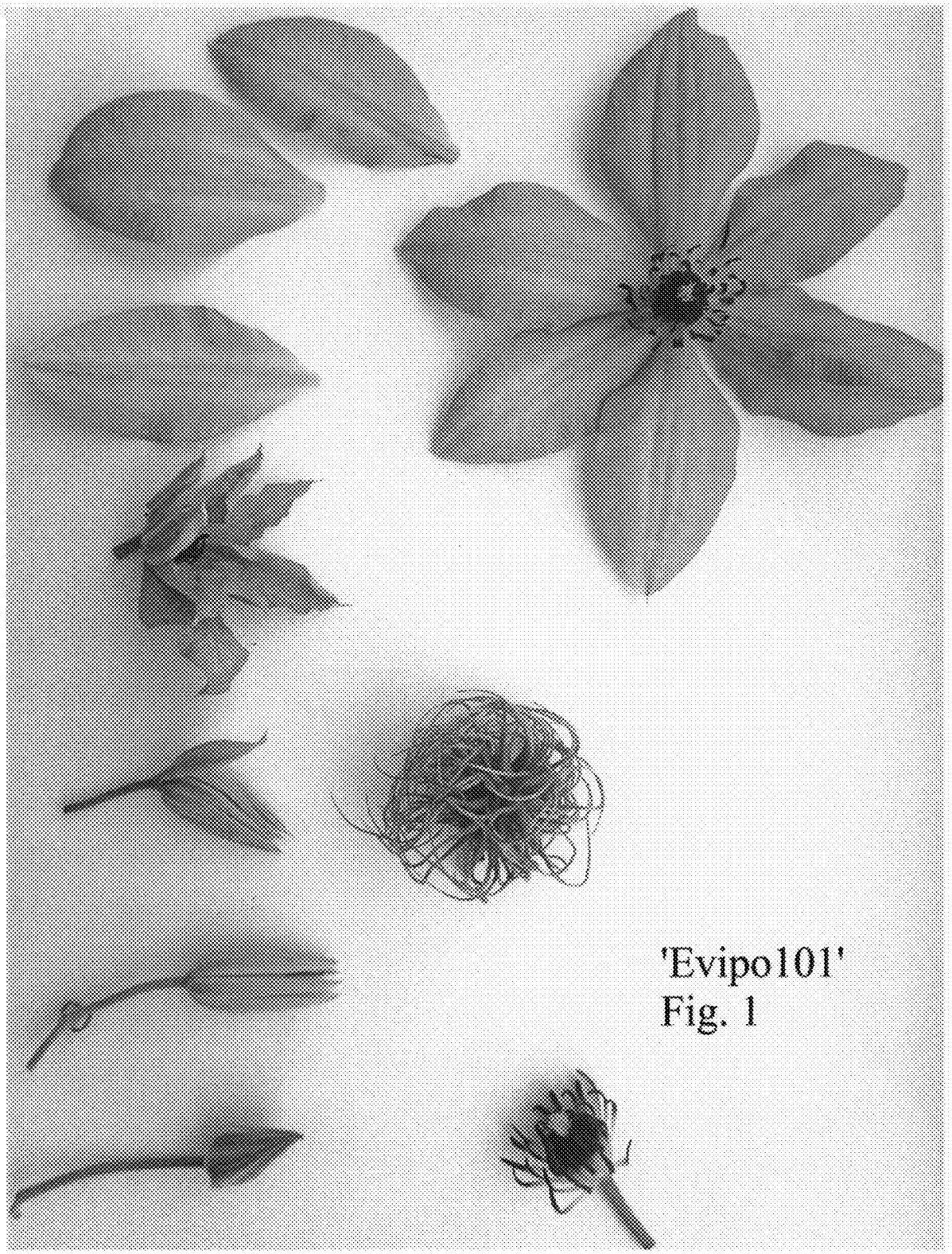
Figure 2:
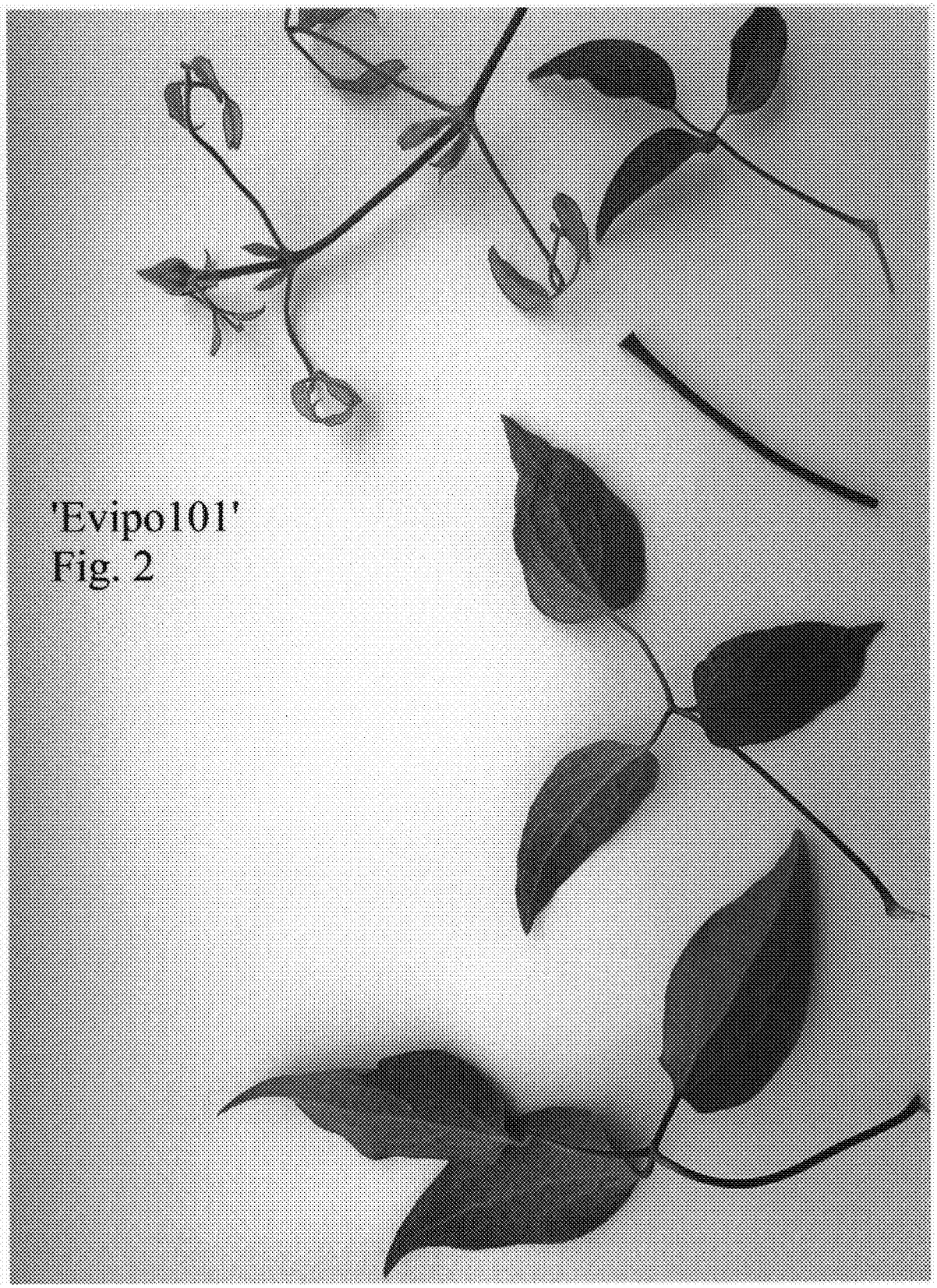
FIG. 2 shows mature and juvenile leaves and stems.

Illustrated plants are 2 years of age.

DETAILED DESCRIPTION OF THE VARIETY

The following is a detailed description of 'Evipo101', as observed in its growth throughout the flowering period in Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo017' described and illustrated in U.S. Plant Pat. No. 15,163 are compared to 'Evipo101' in Chart 1.

CHART 1

| | 'Evipo101' | 'Evipo017' |
|---|---|---|
| Flower diameter | 100 to 120 mm | 100 to 130 mm |
| Tepal upper surface after opening | Violet Group 85A with other intonations of Violet Group 85D. | Violet Group 85A with intonations of Violet Group 85D at the basal zone. |
| Tepal count | Normally 6, occasionally up to 10. | 8 |

Flower and Flower Bud

Blooming habit: Recurrent. The natural flowering period is generally from April to September. Flower buds are formed on current year's growth only.

Flower bud:
- *Size.*—Normally 22 mm in length. Bud diameter is 12 mm.
- *Bud form.*—Elliptic.
- *Bud color.*—Yellow-Green Group 145B with light intonations of Greyed-Red Group 181D at the apex. At ¼ opening the tepals are Violet-Blue Group 91B.
- *Texture.*—Pubescent.

Pedicel:
- *Surface texture.*—Smooth, lightly pubescent.
- *Length.*—On average 25 to 40 mm in length with 2 mm diameter.
- *Color.*—Yellow-Green Group 145A.
- *Strength.*—Moderately strong.

Receptacle:
- *Surface texture.*—Smooth, lightly pubescent.
- *Shape.*—Broad funnel.
- *Size.*—1 mm (h)×3 mm (w).
- *Color.*—Yellow-Green Group 145A.

Flower arrangement:
- *Location on vine.*—New growth only.
- *Borne.*—Singly. Arranged solitary.

Flower bloom:
- *Size.*—100 to 120 mm in diameter and 20 mm in depth.
- *Attitude.*—Outward.
- *Profile.*—Flowers are initially concave, turning to convex as flowers mature.
- *Fragrance.*—None.
- *Lasting quality.*—Flowers normally remain up to 10 days on the plant.
- *General shape.*—Stellate.

Tepals:
- *Tepal color.*—Upon opening, the upper surface is Violet Group 85A with other intonations of Violet Group 85D. The lower surface is Violet Group 85B with a Yellow-Green Group 145B stripe. After opening, the upper surface is Violet Group 85B. The lower surface after opening is Violet Group 85C with a stripe of Yellow-Green Group 145C.
- *Quantity.*—Normally 6 tepals, occasionally up to 10.
- *Size.*—50-60 mm in length by 22-35 mm wide.
- *Overlap.*—Slight to none.
- *Shape.*—Elliptic. The tepal apex is acuminate. The tepal base is typically acute.
- *Apex recurvature.*—Slight.
- *Tepal cross section.*—Flat, very lightly flexed downward.
- *Margins.*—Entire. Some tepals exhibit strong undulations.
- *Persistence.*—Tepals drop off cleanly.

Reproductive parts:
- *Pollen.*—None observed.
- *Anthers.*—Size: 5 mm in length. Color: Greyed-Purple Group 187A. Quantity: On average, 110.
- *Filaments.*—Color: Yellow-White Group 158B. Length: 10 mm.
- *Pistils.*—Quantity: On average, 80.
- *Stigmas.*—Superior in location relative to the length of the filaments and the height of the anthers. Color: Yellow Group 4C.
- *Styles.*—Color: Yellow-Green Group 145C. Length: 15 mm.

Seed head characteristics:
- *Size.*—45 mm in height. 45 mm in diameter.
- *Quantity.*—About 70 seeds per seed head.
- *Style appearance.*—Plumose, semi-erect.

Plant

Plant form: Climbing.

Plant growth: Moderate vigor.

Size: Seasons growth attains 60 to 80 cm in height. Average spread is 50 cm.

Stems:
- *Color.*—Juvenile stems are Greyed-Orange Group 166A. Mature stems are Greyed-Orange Group 166A.
- *Internodes.*—On average, 60 to 80 mm between nodes.
- *Length.*—Normally 20 cm from the base of the plant to the flowering portion of the stem.
- *Diameter.*—About 3 mm.
- *Texture.*—Mature stems are lightly ribbed.

Plant foliage:
- *Leaf characteristics.*—Deciduous.
- *Arrangement.*—Ternate.
- *Leaf size.*—Compound leaves are 90 to 170 mm (l)×70 to 150 mm (w). Leaflets are 35 to 60 mm (l)×15 to 30 mm (w).
- *Abundance.*—On average 2 leaves per 10 cm of stem.
- *Leaf color.*—Juvenile upper Yellow-Green Group 144A with marginal intonations of Greyed-Red Group 179A. Juvenile lower Yellow-Green Group 144A with marginal intonations of Greyed-Red Group 179A. Mature upper Yellow-Green Group 146A. Mature lower Yellow-Green Group 147B.
- *Stipules.*—Absent.
- *Petioles.*—Size: Normally 40 to 75 mm in length by 2 mm diameter. Texture: Lightly pubescent. Color: Greyed-Orange Group 166A.
- *Petioloule.*—Size: 5 to 35 mm in length by 2 mm diameter. Texture: Lightly pubescent. Color: Greyed-Orange Group 166A.
- *Leaflet shape.*—Elliptic. The base is rounded, apex acute.
- *Margin.*—Entire.
- *Surface.*—The upper side is smooth, the lower side is slightly rugose.

*Thickness*.—Moderate.

*Glossiness*.—Not glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo101', substantially as described and illustrated, due to its abundant violet purple flowers with good keepability, attractive long lasting foliage and compact growth, suitability for production from softwood cuttings in pots, durable flowers and foliage which make the variety suitable for distribution in the floral industry.

* * * * *

'Evipo101'

'Evipo101'